United States Patent [19]

Kondo

[11] 4,192,863

[45] Mar. 11, 1980

[54] COMPLETELY ONE-STEP PERMANENT WAVE SOLUTION AND A METHOD FOR USING THE SAME

[76] Inventor: Tokuzo Kondo, 92, Nishi-Koiso, Ohisomachi, Kanagawa Prefecture, Japan

[21] Appl. No.: 587,623

[22] Filed: Jun. 17, 1975

Related U.S. Application Data

[63] Continuation-in-part of Ser. No. 363,735, May 24, 1973, abandoned, which is a continuation-in-part of Ser. No. 735,203, Jun. 7, 1968, abandoned, which is a continuation-in-part of Ser. No. 459,879, May 28, 1965, abandoned, which is a continuation-in-part of Ser. No. 80,758, Jan. 5, 1961, abandoned.

[30] Foreign Application Priority Data

Jun. 12, 1964 [JP] Japan .................................. 39-33015

[51] Int. Cl.² ............................................. A61K 7/09
[52] U.S. Cl. ...................................................... 424/72
[58] Field of Search ........................................... 424/72

[56] References Cited

U.S. PATENT DOCUMENTS

| | | | |
|---|---|---|---|
| 2,631,965 | 3/1953 | Schnell | 424/72 |
| 3,025,218 | 3/1962 | Strain et al. | 424/72 |
| 3,148,126 | 9/1964 | Martin | 424/72 |

FOREIGN PATENT DOCUMENTS 36-299121 1/1961 Japan .......................................... 424/72

OTHER PUBLICATIONS

*Chem. Abstracts,* vol. 56 (1962), 6106(c).

*Primary Examiner*—Frederick E. Waddell
*Attorney, Agent, or Firm*—Haseltine, Lake & Waters

[57] ABSTRACT

A completely one-step permanent wave solution which is harmless and effective on hair to provide odorless, non-porous and silky and intrinsic permanent wave hair and consisting of ammonium thioglycolate, oxy-organic acid, ethyl alcohol, caustic alkali, ammonia water, organic amines and water. The solution is applied to the hair and does not require an oxidizing treatment.

6 Claims, No Drawings

COMPLETELY ONE-STEP PERMANENT WAVE SOLUTION AND A METHOD FOR USING THE SAME

CROSS-RELATED APPLICATIONS

This application is a continuation-in-part of copending Application Ser. No. 363,735 filed May 24, 1973, now abandoned, which in turn is a continuation-in-part of application Ser. No. 735,203 filed June 7, 1968 and now abandoned, in turn a continuation-in-part of Ser. No. 459,879 filed May 28, 1965 and now abandoned, in turn a continuation-in-part of Ser. No. 80,758 filed Jan. 5, 1961 and now abandoned.

FIELD OF THE INVENTION

The present invention relates to a one-step permanent wave solution and to a method for using the same, and particularly to an improvement in the one-step permanent wave solution of the present inventors's Japanese Pat. No. 299,121 by increasing the content of oxy-organic acid from 0.01–0.03% to 0.1–0.4% by weight and adding an emulsifier of monoethanolamine, diethanolamine, triethanolamine or a mixture thereof in an amount of 0.01 to 1.0% by weight of the solution.

BACKGROUND

The permanent wave solutions now widely employed in the world are classified into the following two main groups in respect of the application method.

(1) Two-step permanent wave solution.

This solution is widely employed in professional beauty parlors and the application method comprises tightly winding on about 60 to 100 rods having diameters of about 2 to 10 mm, hair which is coated with a first solution practically containing 5 to 8% by weight of alkali thioglycolate or a modification thereof as a main component. This winding operation takes about 20 minutes. Then the wound hair is again coated with the aforesaid solution and a vinyl cap is placed on the head of the user for about 10 to 30 minutes until the solution is dissolved and softens the hair surface. Then the hair is coated with a second solution containing about 2 to 6% by weight of a strong oxidizing agent such as potassium bromate, sodium bromate, hydrogen peroxide, or the like, or with oxygen gas for about 20 to 30 minutes to fix and deodorize the dissolved and softened hair. The hair is then unwound from the rods and subjected to a warm-rinse for about 5 to 10 minutes. The hair is then coated with a hair setting lotion and wound on 30 to 60 curling rollers having diameters of 1 to 3 cm to produce large curls of 2 to 6 cm diameter according to preference. This takes about 20 minutes. The hair is then dried with hot air at a temperature of about 45° C. for about 25 minutes, after which the hair is unwound from the rollers, and brushed and arranged with a comb and hairpins to complete the hair-dressing.

(2) One-step permanent wave solution.

This solution comprises almost the same composition as that of the above-mentioned first solution which dissolves and softens the hair and the application method thereof in professional beauty parlors necessarily employs the above-mentioned second solution to remove the bad smell of hydrogen sulfide and the like produced by the decomposition of the thioglycolate when applied. Otherwise, the bad smell cannot be removed at one time and it becomes necessary to fully water-rinse the hair and to subject the hair to natural deodorization in air for about four weeks. Accordingly, the conventional one-step permanent wave solutions are not true one-step ones but actually belong to the two-step solutions.

As seen from the above, the conventional two-step or one-step permanent solutions takes at least 120 minutes to complete the permanent waving and such a long application period represents a troublesome drawback.

Furthermore, the conventional permanent wave solutions generally contain 1 to 10% by weight of thioglycolic acid for dissolving and softening the hair whereby cystine and by-products of cysteine contained in the hair dissolve out and react with the second solution to inevitably produce hydrogen cyanide and other cyano compounds as pollutants which can produce chemical poisoning, such as pernicious anemia, cirrhosis of the liver or the like, and the thioglycolic acid retained in the hair renders the hair porous, coarse, non-sleek and discolored.

Permanent wave solutions are disclosed in U.S. Pat. Nos. 3,025,218 (Strain et al), 2,631,965 (Schnell) and 3,148,126 (Martin).

In U.S. Pat. No. 3,025,218, a large amount of oxyorganic acid of tartaric acid is used only for lowering the pH of the permanent wave solution but still causing the dissolved and softened hair to have a bad smell, and accordingly, a setting agent for the oxidation is required whereby the applied hair is greatly damaged. In U.S. Pat. No. 2,631,965, 1 to 10% by weight of thioglycolic acid and a large amount of oxy-organic ammonium salt are contained in alkaline aqueous solution, the hair is discolored and a bad smell is produced, and for quick deodorization in beauty parlors, it is necessary to use a setting agent for oxidation to remove the bad smell and accordingly, the solution is actually a two-step solution which damages the hair. In U.S. Pat. No. 3,148,126, the permanent wave solution contains 1 to 15% by weight of thioglycolate and monoethanolamine, and still requires a setting agent for oxidation (containing hydrogen peroxide and tartaric acid), heating at a high temperature of 150° to 200° F. or delivering oxygen gas under a helmet covering the scalp for quick deodorization and wave fixing. Accordingly, this permanent wave solution properly belongs to the two-step solution whereby the applied hair is greatly damaged.

The present inventor has made a special study of hair damage due to the application of the conventional permanent wave solutions and has obtained Japanese Pat. No. 299,121. He has further improved the permanent wave solution according to Japanese Pat. No. 299,121 to arrive at the present invention. The permanent wave solution of Japanese Pat. No. 299,121 is a completely one-step permanent wave solution comprising 3 to 3.5% by weight of thioglycolic acid, 0.01 to 0.03% by weight of oxy-organic acid and 1 to 2% by weight of ethyl alcohol, and caustic alkali in an amount of 0.1% or less by weight is added to adjust the pH of the solution to 7.0 to 11.0.

SUMMARY OF THE INVENTION

The present inventor has found that surprisingly superior effects with respect to deodorization and waving are obtained by particularly enriching the above contents of oxyorganic acid from 0.01–0.03% to 0.1–0.4% by weight and adding an emulsifier of monoethanolamine, diethanolamine, triethanolamine or a mixture thereof in an amount of 0.01–1.0% by weight of the solution and 1.0–10.0% by weight of ethyl alcohol. The present invention is based on the following hair waving theory.

It has been considered that conventional permenent waving is carried out by cutting off the sulfur linking (—S—S—) of cystine $$\begin{pmatrix} S-CH_2CH(NH_2)COOH \\ | \\ S-CH_2CH(NH_2)COOH \end{pmatrix}$$

in keratin, which is a kind of protein and constitutes hair, by means of hydrogen atoms contained in the first solution (a reducing agent such as thioglycolic acid) to produce cysteine (HS—CH$_2$CH(NH$_2$)COOH) which can be easily curled, and then by fixing by means of oxygen atoms contained in the second solution (an oxidizing agent such as potassium bromate, etc.) to recover the sulfur linking, as shown in the following formula:

$$\underset{\text{Sulfur linking}}{-S-S-} + \underset{\text{Hydrogen}}{2H} \longrightarrow \underset{\text{Cysteine}}{-S-H \quad H-S-}$$

$$\xrightarrow{+O} \underset{\text{Sulfur linking}}{-S-S-} + \underset{\text{Water}}{H_2O}$$

In the above case, the reducing agent of thioglycolic acid is employed in an amount of 1 to 10% by weight of the solution but when employed in an amount below 5%, it has been considered that cutting off of the sulfur linking of cystine could be possible by heating.

However, the present inventor has found that the above waving theory is in error because it is common knowledge that it is difficult to effect the hydrogenation of an amino acid in an alkaline solution. In fact, the first solution dissolves out part of the cystine to effect softening but it also causes porousness, fineness, non-sleekness and discoloration of the hair. The hair is then curled and fixed, as a common property of protein, by means of the oxidizing agent of the second solution. At the same time, the dissolved cystine or its derivatives are reacted with an excess amount of the oxidizing agent of the second solution to produce sulfites and cyanides which immediately change to hydrogen cyanide (HCN) effecting chemical poisoning by reacting with carbon dioxide gas and water in the air. Further, it is necessary to rinse the treated hair to remove the produced hydrogen cyanide and the bad smell of hydrogen sulfide and the like.

On the other hand, the permanent waving of the present invention is carried out in a short time without the second solution but by homogeneously hydrolyzing in the presence of the ethyl alcohol to cut off the sulfur linking of the cystine as follows:

$$\underset{\text{Sulfur linking}}{-S-S-} + \underset{\text{Water}}{H_2O} \xrightarrow{\text{Hydrolysis}}$$
$$\underset{\text{Cut sulfur linking}}{-S-H \quad H-O-S-}$$

The resulting cut sulfur linking effects an intramolecular slip by a curling process and is dehydrated when dried to recover the sulfur linking for fixing, as follows:

$$\underset{\text{Cut sulfur linking}}{-S-H \quad H-O-S-} \xrightarrow{-H_2O} \underset{\text{Sulfur linking}}{-S-S-}$$

In this case, the generation of hydrogen sulfide (H$_2$S) from thioglocylic acid can be prevented by the adsorption of the organic amine and ethyl alcohol contained in the permanent wave solution of the present invention.

Further, owing to the fact that no application of an oxidizing agent is made to the hair, the present wave solution never generates hydrogen cyanide and neither damages the hair nor causes the porousness of the hair, while also the production cost becomes very low.

In short, the present invention can not be seen to flow from the prior art, and the unique and characteristic advantages of the present invention are as follows:

(i) The permanent wave solution of the present invention provides truly elastic non-damaged, non-porous, sleek and creamy waved hair in a short time, such as an overall time within one hour, without regard to the kind and state of the hair, while the conventional permanent wave solutions need an overall time of 2 hours, or more, for all processes (coating, winding, further coating, vinylcapping, oxidizing or deodorizing, rinsing, rewinding, and drying steps) and it still causes all types of hair to be rendered porous and/or discolored.

(ii) The permanent wave solution of the present invention is harmless and never results in chemical poisoning with cyano compounds and the like because there is no generation of the poisonous compounds arising from the use of an oxidizing agent and/or neutralizing agent. The conventional permanent wave solutions inevitably effect chemical poisoning, such as, pernicious anemia, cirrhosis of the liver or the like due to the cyano compounds, hydrogen sulfide and the like generated in the course of the permanent waving processes.

(iii) The permanent wave solution of the present invention is most effective and substantially odorless when used because of the synergistic action of a small amount of ethyl alcohol and a very small amount of tartaric acid or citric acid and also a very small amount of monoethanolamine, diethanolamine, triethanolamine, or a mixture thereof, whereas the conventional permanent wave solutions never simultaneously contain ethyl alcohol, oxy-organic acid and the monoethanolamine or the like; the conventional solutions cause the discoloration of the hair and produce the bad smell of hydrogen sulfide and further poisoning cyano compounds when the oxidizing agent is applied which can be injurious to human health in repeated applications and can damage the beauticians' finger tips, finger nails and also damage the hair in a single use to produce a rough touch and affording no gloss.

(iv) Hairdyeing can be carried out in advance to provide brilliantly colored hair without discoloration due to the application of the permanent wave solution of the present invention immediately after the hairdyeing, while the conventional permanent wave solutions can never be applied immediately after the hairdyeing because the wave solutions positively dissolve the surface of the dyed hair.

The permanent wave solution of the present invention is prepared by mixing 2–5% by weight of ammonium thioglycolate (approximately 1.7–4.2% by weight of thioglycolic acid) as a hydrolysis-promoting and hair-softening agent, 0.01–1.0% by weight of organic amines such as monoethanolamine, diethanolamine, triethanolamine or a mixture thereof as an emulsifier having hydrolyzing and volatile gas-adsorbing properties, 0.1–0.4% by weight of an oxy-organic acid such as tartaric acid or citric acid as a hair-softening, hydrolyzing and permeability-promoting agent, 1.0–10.0% by weight of ethyl alcohol as a hydrolyzing intramolecular dehydrating, deodorizing and permeability-promoting agent, 0.02–0.10% by weight of caustic alkali such as caustic potash or caustic soda as a hydrolyzing agent and 1.0–2.4% by weight of 28% ammonia water as a hydrolyzing and exothermic hair-swelling agent and water as a remainder and adjusting the pH of the mixture to 7.0 to 9.6. Such solution can provide, for the first time, a completely one-step permanent wave solution which can promptly cut off the sulfur linking of the cystine in the hair and recover the sulfur linking by intramolecular dehydration for fixing after hair molecular slip, by a curling process.

An ammonium thioglycolate content of less than 2.0% by weight has little effect on the hair and a content of more than 5.0% by weight brings about the bad smell of hydrogen sulfide and the like and causes hair damage. The ammonium thioglycolate can be substituted by thioglycolic acid and ammonia. A caustic alkali content of more than 0.1% by weight produces fading and damage to the hair. Ethyl alcohol of more than 10.0% by weight causes great volatility of the solution and effects uneven waving and a content of less than 1.0% by weight has little effect on the hair and results in bad smell from the hair. In the absence of ethyl alcohol, the composition, otherwise constituted, acts on the hair to provide a substantially bad smell, no elasticity, uneven weak curls and no sleekness. An ammonia water (28%) content of more than 2.4% by weight causes hair damage and a content of less than 1.0% by weight has little effect on the hair. An organic amine content of more than 1.0% by weight produces a rough touch and no gloss of the hair as well as hair damage, while a content of 0.01% or more by weight is effective and free of difficulties.

All the known conventional permanent wave solutions do not simultaneously contain ethyl alcohol, oxy-organic acid and the organic amine, and accordingly, even in the known one-step processes, except in that of the present inventor's Japanese Pat. No. 299,121, the processed hair has a bad smell for at least one month even after washing the hair several times. (The hair processed with the permanent solution of Japanese Pat. No. 299,121 can be deodorized after several days.) For such reason, the conventional one-step processes in practice require the second solution of oxidizing agent to deodorize the bad smell. By way of example, a maximum amount of about 100 times the NaOH amount of the present invention is used in Examples 11 and 12 of U.S. Pat. No. 2,631,965 (Schnell). Such use of alkali in large amounts results in non-sleekness, non-flexibility and stiffness of the waved hairs as well as irritation of skin.

In order to avoid such drawbacks, the use of several times the amount of tartaric or citric acid as employed in the present invention becomes necessary, but effects a discoloration of the hair. Further, the thioglycolic acid used as the hair-softening agent is used in larger amounts of about 6% by weight and causes damage to the waved hairs and the residual bad smell of hydrogen sulfide and the like from the waved hairs, which in practice required the need for a second solution of an oxidizing agent and/or deodorizing agent to deodorize the waved hair.

In order to remove the above drawbacks in the conventional one-step and two-step processes, the amount of thioglycolic acid in the present invention has been limited to 1.7–4.2% by weight and the caustic potash or caustic soda limited to 0.02–0.10% by weight, owing to additional 1.0–10.0% by weight of ethyl alcohol, 0.01–1.0% by weight of monoethanolamine, diethanolamine, triethanolamine or a mixture thereof, 1.0–2.4% by weight of 28% ammonia water and oxy-organic acid with adjustment of the pH to 7.0–9.6, whereby the oxy-organic acid amount of tartaric acid or citric acid to provide the waved hairs with sleekness, flexibility, elasticity and fragrance can be limited to only 0.10–0.40% by weight.

The method of the invention can be used in beauty parlors as follows:

(1) The hair is tightly wound in the desired hair style on about 60 to 100 rods or rollers having diameters of 2 to 20 mm and fastened with rubber bands while optionally coating 50 ml. of the permanent wave solution of the present invention in about 20 minutes. The wound hair is then coated with another 50 ml. of the solution.

(2) The head of the user is covered with a vinyl cap for about 10 to 20 minutes and then the cap is removed.

(3) The hair as wound is rinsed with warm water and wiped with a towel, then the hair is dried naturally while it is removed from the rods or rollers. The setting is then completed by combing preferably with a hand dryer while taking advantage of residual moisture over a total required time of about 10 minutes.

(4) Instead of drying naturally in the above step (3) hot air of about 45° C. from a dryer can be applied to the hair for about 15 minutes, and if desired, all the hair, or a part of the hair such as that at the front, crown and nape are taken off the rods and rollers and tightly rewound on rollers having diameters of 1 to 3 cm whereafter again hot air is applied to the hair for about 5 minutes to produce desired large curls. Even after washing, the large curls retain almost the same diameters as those of the rollers.

The over all time required in the method of the present invention is within about 60 minutes which is substantially less than those employing conventional permanent wave solutions.

As other compounding agents, there can be added perfume, coloring agents and the like.

According to the above processes, it becomes possible to quite easily obtain within about 1 hour, substantially odorless, silky, non-porous and non-damaged permanently curled hair having a curl diameter of 2 to 6 cm which is particularly appreciated from a beauty viewpoint even after washing the hair 4 to 6 months later, without the necessity of a setting process, and further without the chemical poisoning with cyano compounds or the like as in the processes using the conventional permanent wave solutions.

The permanent wave solution of the present invention can also be applied to naturally crimped hair to change it into permanently straight hair and also it can be utilized to make silky brilliant hair pieces and wigs or to finish hair waving in making dolls.

DESCRIPTION OF PREFERRED EMBODIMENTS

The following examples are illustrative of permanent wave solutions of the present invention and which are prepared at room temperature by mixing the constituents with one another. It will be understood that various other solutions may be made following the guiding principles and teachings contained herein, and the examples set forth herein are, therefore, in no way to be regarded as limitative of the full scope of the present invention.

EXAMPLE 1

| | |
|---|---|
| Ammonium thioglycolate (50% acid*) | 3.4 g (1.7 g as acid and corresponds to 2.0 g as pure ammonium thioglycolate) |
| Tartaric acid or citric acid | 0.1 g |
| Ethyl Alcohol | 1.0 g |
| Monoethanolamine, diethanolamine, triethanolamine or a mixture thereof | 0.01 g |
| Caustic potash or caustic soda | 0.02 g |
| 28% Ammonia water | 1.0 g |
| Distilled water | 94.47 g |

*Ammonium thioglycolate contained 50% of acid calculated as thioglycolic acid.

EXAMPLE 2

| | |
|---|---|
| Ammonium thioglycolate (50% acid) | 4.0 g (2.0 g as acid and corresponds to 2.37 g as pure ammonium thioglycolate) |
| Tartaric acid or citric acid | 0.15 g |
| Ethyl alcohol | 1.0 g |
| Monoethanolamine, diethanolamine, triethanolamine or a mixture thereof | 0.03 g |
| Caustic potash or caustic soda | gg |
| 28% Ammonia water | 2.0 g |
| Distilled water | 92.738 92.738 |

EXAMPLE 3

| | |
|---|---|
| Ammonium thioglycolate (50% acid) | 6.4 g (3.2 g as acid and corresponds to 3.78 g as pure ammonium thioglycolate) |
| Tartaric acid or citric acid | 0.15 g |
| Ethyl alcohol | 1.0 g |
| Monoethanolamine, diethanolamine, triethanolamine or a mixture thereof | 0.03 g |
| Caustic potash or caustic soda | 0.082 g |
| 28% Ammonia water | 2.0 g |
| Distilled water | 90.338 g |

EXAMPLE 4

| | |
|---|---|
| Ammonium thioglycolate (50% acid) | 6.4 g (3.2 g as acid and corresponds to 3.78 g as pure ammonium thioglycolate) |
| Tartaric acid or citric acid | 0.2 g |
| Ethyl alcohol | 1.5 g |
| Monoethanolamine, diethanolamine, triethanolamine or a mixture thereof | 0.04 g |
| Caustic potash or caustic soda | 0.07 g |
| 28% Ammonia water | 2.0 g |
| Distilled water | 89.79 g |

EXAMPLE 5

| | |
|---|---|
| Ammonium thioglycolate (50% acid) | 6.4 g (3.2 g as acid and corresponds to 3.78 g as pure ammonium thioglycolate) |
| Tartaric acid or citric acid | 0.1 g |
| Ethyl alcohol | 1.0 g |
| Monoethanolamine, diethanolamine, triethanolamine or a mixture thereof | 0.89 g |
| Caustic potash or caustic soda | 0.08 g |
| 28% Ammonia water | 1.68 g |
| Distilled water | 89.85 g |

EXAMPLE 6

| | |
|---|---|
| Ammonium thioglycolate (50% acid) | 6.4 g (3.2 g as acid and corresponds to 3.78 g as pure ammonium thioglycolate) |
| Tartaric acid or citric acid | 0.2 g |
| Ethyl alcohol | 5.0 g |
| Monoethanolamine, diethanolamine, triethanolamine or a mixture thereof | 0.89 g |
| Caustic potash or caustic soda | 0.07 g |
| 28% Ammonia water | 1.68 g |
| Distilled water | 85.76 g |

EXAMPLE 7

| | |
|---|---|
| Ammonium thioglycolate (50% acid) | 8.0 g (4.0 g as acid and corresponds to 4.74 g as pure ammonium thioglycolate) |
| Tartaric acid or citric acid | 0.15 g |
| Ethyl alcohol | 3.0 g |
| Monoethanolamine, diethanolamine, triethanolamine or a mixture thereof | 0.03 g |
| Caustic potash or caustic soda | 0.082 g |
| 28% Ammonia water | 2.0 g |
| Distilled water | 86.738 g |

EXAMPLE 8

| | |
|---|---|
| Ammonium thioglycolate (50% acid) | 8.4 g (4.2 g as acid and corresponds to 5.0 g as pure ammonium thioglycolate) |
| Tartaric acid or citric acid | 0.4 g |
| Ethyl alcohol | 10.0 g |
| Monoethanolamine, diethanolamine, triethanolamine or a mixture thereof | 1.0 g |
| Caustic potash or caustic soda | 0.1 g |
| 28% Ammonia water | 2.4 g |
| Distilled water | 77.7 g |

What is claimed is:

1. A permanent wave solution which consists of in percent by weight; ammonium thioglycolate 2.0 to 5.0%; tartaric acid or citric acid 0.10 to 0.40%; ethyl alcohol 1.0 to 10.0%; caustic potash or caustic soda 0.02 to 0.10%; 28% ammonia water 1.0 to 2.4%; monoethanolamine, diethanolamine, triethanolamine or mixtures thereof 0.01 to 1.0%; and distilled water as the remainder, said solution being adjusted to a pH of 7.0 to 9.6.

2. The permanent wave solution of claim 1 which consists in weight percent of; ammonium thioglycolate 3.78%; tartaric acid or citric acid 0.15%; ethyl alcohol 1.0%; caustic potash or caustic soda 0.082%; 28% ammonia water 2.0%; monoethanolamine, diethanolamine, triethanolamine or mixtures thereof 0.03% and distilled water as the remainder.

3. The permanent wave solution of claim 1 which consists in weight percent of; ammonium thioglycolate 3.78%; tartaric acid or citric acid 0.2%; ethyl alcohol 1.5%; caustic potash or caustic soda 0.07%; 28% ammonia water 2.0%; monoethanolamine, diethanolamine, triethanolamine or mixtures thereof 0.04% and distilled water as the remainder.

4. The permanent wave solution of claim 1 which consists in weight percent of; ammonium thioglycolate 3.78%; tartaric acid or citric acid 0.1%; ethyl alcohol 1.0%; caustic potash or caustic soda 0.08%; 28% ammonia water 1.68%; monoethanolamine, diethanolamine, triethanolamine or mixtures thereof 0.89% and distilled water as the remainder.

5. The permanent wave solution of claim 1 which consists in weight percent of; ammonium thioglycolate 3.78%; tartaric acid or citric acid 0.2%; ethyl alcohol 5.0%; caustic potash or caustic soda 0.07%; 28% ammonia water 1.68%; monoethanolamine, diethanolamine, triethanolamine or mixtures thereof 0.89% and distilled water as the remainder.

6. The process of giving permanent shape to hair which comprises arranging the hair in a desired style and applying to the hair the permanent wave solution of claim 1 in an amount sufficient to moisten the hair.

* * * * *